Dec. 17, 1963 P. SHAMBURGER Plant Pat. 2,329
ROSE PLANT
Filed Jan. 10, 1963
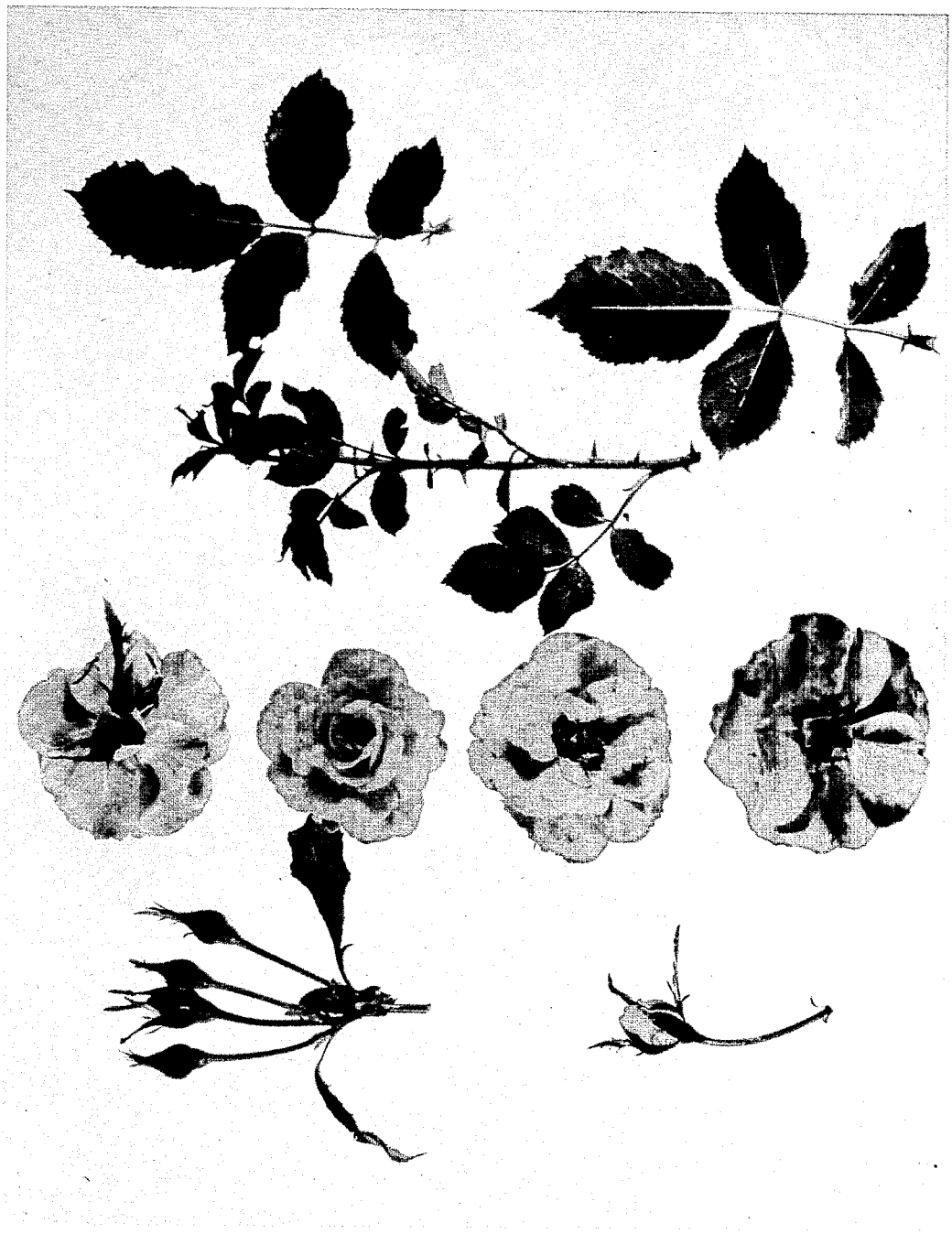
Inventor.
Paul Shamburger
By: Robb & Robb
Attorneys.

United States Patent Office

Plant Pat. 2,329
Patented Dec. 17, 1963

2,329

ROSE PLANT

Paul Shamburger, Tyler, Tex., assignor to The Conard-Pyle Company, West Grove, Pa., a corporation of Pennsylvania

Filed Jan. 10, 1963, Ser. No. 250,723
1 Claim. (Cl. Plt.—6)

The present invention relates to a new and distinct variety of rose plant of the climbing floribunda class, which originated as a cultivated sport of the variety "Climbing Floradora" (Plant Patent No. 1,054).

This new variety was discovered by me in my own rose growing fields near Tyler, Texas, where I was growing plants of the parent variety, "Climbing Floradora." At the time of my discovery aforementioned, my attention was attracted to one particular plant amongst those of the "Climbing Floradora" variety by the fact that the plant bore flowers, foliage and prickles which were distinctly different from those normally found on the "Climbing Floradora" variety. Upon closer examination of the plant, I found that it had sported, and I thereupon took steps to preserve the sport, keep it under observation, and to later asexually reproduce the same. My continued observations of the original plant and the asexually reproduced progeny thereof, as produced by me by budding at Tyler, Texas, fully confirmed the unique characteristics of the sport and conclusively established that these characteristics come true to form and are transmissible through succeeding propagations.

My new variety is essentially distinguished from its parent variety "Climbing Floradora," by having a darker flower color corresponding in general color effect to Carmine, which is free from the bluish undertones of the mature blooms of "Climbing Floradora," as well as by foliage which is dully and leathery, contrary to the shiny foliage of the parent variety, and by prickles which are straight-pointed in contrast to the downwardly hooked prickles of "Climbing Floradora."

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with the Horticultural Color Chart of the Royal Horticultural Society, except where general color terms of ordinary dictionary significance are obvious:

Type: Hardy; pillar; outdoor; sport; for garden decoration.
Class: Climbing floribunda.
Parentage: Sport of "Climbing Floradora."
Propagation: Holds its distinguishing characteristics through succeeding propagations by budding.

*Flower*

Locality where grown and observed: West Grove, Pennsylvania.
Flowers Borne: Several to stem; in regular clusters; on short stems of normal strength.
Quantity of bloom: Abundant, outdoors.
Continuity: Continuous.
Fragrance: Slight.
Bud:
*Peduncle.*—Medium length; medium caliper; erect; rough; with numerous Reddish Brown hairs. Color—Fern Green, Plate 0862, overlaid with Garnet Brown, Plate 00918/1.
*Before calyx breaks.*—Size—small. Form—short; ovoid; with a conspecuous neck; with foliaceous appendages on the surface of the bud; with slender, bristle-like foliaceous parts extending beyond the tip of the bud equal to ¼ or more of its length.
*As calyx breaks.*—Color—Spinel Red, Plate 0023.
*As first petal opens.*—Size—small. Form—medium short; ovoid. Color—outside: near Crimson, Plate 22/1; inside: near Carmine, Plate 21.
*Opening.*—Opens up well.

Bloom:
*Size (when fully open).*—From small to medium size; from 2 inches to 2½ inches.
*Petalage.*—Double; from 30 to 35 petals; arranged regularly.
*Form.*—Cupped at first, but becoming flat; petals being at first loosely rolled outward and remaining loosely rolled outward at maturity.
Petals:
*Texture.*—Medium thickness; soft.
*Apppearance.*—Inside—satiny. Outside—shiny.
*Shape.*—Outer petals—roundly obovate; scalloped; with apex flat. Intermediate petals—obovate; scalloped; with apex flat. Inner petals—obovate.

This description of a newly opened flower was made from a rose grown outdoors during the month of July at West Grove, Pennsylvania:
*Color.*—Outer petal—outside surface: near Rose Madder, Plate 23/1, with point of attachment Pod Green, Plate 061/2; Inner surface: between Carmine, Plate 21, and Carmine, Plate 21/1, with a narrow zone of Magnolia Purple, Plate 030/1 surrounding the point of attachment. Intermediate petal—outside surface: near Rose Madder, Plate 23/1, with point of attachment near Pod Green, Plate 061/3; inside surface: Carmine, Plate 21/1, slightly tinted with Magnolia Purple, Plate 030/2 toward base of petal. Inner petal—outside surface: China Rose, Plate 024; inside surface: near Claret Rose, Plate 021.

This description was made from a rose that was open for three days outdoors during the month of July, at West Grove, Pennsylvania:
*Color.*—Outer petal—outside surface: China Rose, Plate 024/1; inside surface: Crimson, Plate 22/1, grading to Magenta, Plate 27/2 toward base of petal. Inner petal—outside surface: China Rose, Plate 024/1, with point of attachment near White; inside surface: Carmine, Plate 21, grading to Spiraea Red, Plate 025/1 over basal ¼ of petal, with point of attachment Phlox Pink, Plate 625/3.
*General color effect.*—Newly opened flower—Carmine, Plate 21. 3 days open—Carmine, Plate 21.
*Behavior.*—Drop off cleanly.
*Flower longevity.*—On bush in garden—5 days in July. Cut roses grown outdoors and kept at living room temperatures—2 days in July.

*Reproductive Organs*

Stamens: Medium number; arranged irregularly about pistils; mixed with petaloids.
Filaments: Moderate number; short; most with anthers. Color—Mimosa Yellow, Plate 602, at base, becoming overlaid with Jasper Red, Plate 018.
Anthers: Open at various times; small; occasionally an anther fused with a petaloid. Color—Spanish Orange, Plate 010.
Pollen: Sparse. Color—Gold.
Pistils: Few.
Styles: Uneven; medium length; thin; bunched.
Stigma: Color—Whitish Yellow.
Ovaries: All enclosed in receptacle.
Hips: None observed.
Sepals: Permanent; moderately long; spear-shaped; recurved.

Seeds: None observed.

*Plant*

Foliage:

*Leaves.*—Compound of 3–5 leaflets; abundant quantity; moderately large; moderately heavy; leathery; wrinkled margin.

*Leaflets.*—Shape—oval, with apex acute. Base—obtuse. Margin—simply serrate.

*Color.*—Mature—Upper surface: Spinach Green, Plate 0960; under surface: Spinach Green, Plate 0960/2. Young—upper surface: near Purple Madder, Plate 1028/2, overlying Spinach Green, Plate 0960/1; under surface: near Purple Madder, Plate 1028/2.

*Rachis (the supporting stem of the compound leaf).* — Light. Upper side — grooved; hairy. Under side—sparsely prickly.

*Stipules.*—Moderately short; narrow; with short points turning out at an angle of more or less 45°.

*Disease resistance.*—Resistant to mildew and black-spot comparable to that of the average rose variety grown under the same cultural conditions at West Grove, Pennsylvania.

Growth:

*Habit.*—Bushy; upright; much-branched.

*Growth.*—Vigorous.

*Canes.*—Medium caliper.

*Main stems.*—Dull. Color—Fern Green, Plate 0862/1, lightly overlaid with Garnet Brown, Plate 00918/2 on side facing sun. Prickles—many; straight; color: Garnet Brown, Plate 00918/3. Hairs—none.

*Branches.*—Dull. Color—Fern Green, Plate 0862/1. Prickles—many, straight; color: Garnet Brown, Plate 00918/3, overlying Fern Green, Plate 0862/1. Hairs—several, glandular; color: Brown.

Growth:

*New shoots.*—Dull. Color—Fern Green, Plate 0862/1. Prickles—many; straight; color: varies from Fern Green, Plate 0862/1 to near Garnet Brown, Plate 00918/3. Hairs—several, glandular; color: Brown.

I claim:

A new and distinct variety of rose plant of the climbing floribunda class, substantially as herein shown and described, characterized particularly as to novelty by the unique combination of dull and leathery foliage, straight prickles, and a distinctive and attractive general color tonality of the flowers which are darker than the flowers of the parent variety "Climbing Floradora" (Plant Patent No. 1,054), said general color tonality corresponding to Carmine and being free from the usual bluish undertones of the mature blooms of "Climbing Floradora."

No references cited.